United States Patent [19]

Raabe et al.

[11] 4,066,768
[45] Jan. 3, 1978

[54] DERIVATIVES OF 1-PHENOXY-3-AMINO-PROPAN-2-OL

[75] Inventors: Thomas Raabe, Rodenbach; Otto Gräwinger, Frankfurt am Main; Josef Scholtholt, Mittelbuchen; Rolf-Eberhard Nitz, Bergen-Enkheim; Eckhard Schraven, Frankfurt am Main, all of Germany

[73] Assignee: Cassella Farbwerke Mainkur Aktiengesellschaft, Germany

[21] Appl. No.: 669,995

[22] Filed: Mar. 24, 1976

Related U.S. Application Data

[63] Continuation-in-part of Ser. No. 531,344, Dec. 10, 1974.

[30] Foreign Application Priority Data

Dec. 27, 1973 Luxembourg ................... 34590

[51] Int. Cl.$^2$ .................. A61K 31/44; C07D 213/36
[52] U.S. Cl. ........................... 424/263; 542/424; 260/295 D; 260/295 S; 260/296 AE; 260/256.4 R
[58] Field of Search ........ 260/296 AE, 295 K, 295 E, 260/295 S; 424/263

[56] References Cited

U.S. PATENT DOCUMENTS

| | | | |
|---|---|---|---|
| 3,830,806 | 8/1974 | Raabe et al. ................. | 260/240 J |
| 3,852,291 | 12/1974 | Augstein et al. ............. | 260/256.4 C |
| 3,940,406 | 2/1976 | Raabe et al. ................. | 260/296 AE |
| 3,969,363 | 7/1976 | Raabe et al. ................. | 260/296 AE |

Primary Examiner—Alan L. Rotman
Attorney, Agent, or Firm—Berman, Aisenberg & Platt

[57] ABSTRACT

The present invention relates to new pharmacologically valuable derivatives of 1-phenoxy-3-amino-propan-2-ol having the formula

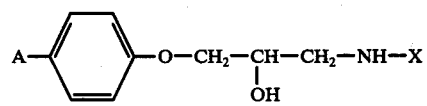

wherein X denotes

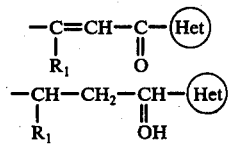

A denotes —CH$_2$—alkoxy, —O—alkoxyalkyl, —O—hydroxyalkyl or

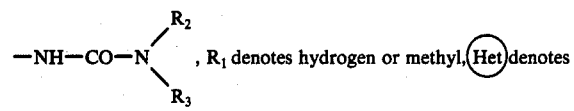

, R$_1$ denotes hydrogen or methyl, (Het) denotes an aromatic or quasi-aromatic, 5-membered or 6-membered, monocyclic ring which is linked through a C atom which has one or 2 nitrogen, oxygen and/or sulphur hetero-atoms and which can be substituted additionally by one or more methyl groups, and R$_2$ and R$_3$ denote hydrogen, alkyl, alkenyl or cycloalkyl or, conjointly with the N atom to which they are linked, and optionally with a further oxygen or sulphur hetero-atom, denote a saturated, 5-membered or 6-membered, monocyclic, heterocyclic structure, and alkyl radicals contain 1 to 4 carbon atoms, alkoxy radicals contain 1 to 4 carbon atoms, alkenyl radicals contain 3 to 4 carbon atoms and cycloalkyl radicals contain 5 to 7 carbon atoms; and aldehyde condensation products and acid addition salts thereof and to the production thereof by a method selected from (A) reacting a compound having the formula

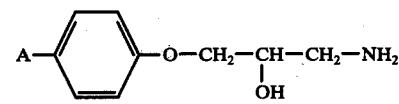

with a compound of the general formula Y — X wherein X has the meanings indicated above and Y represents halogen and, if X denotes

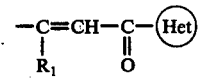

also represents —OH, —OK and —ONa; (B) reacting a compound having the formula

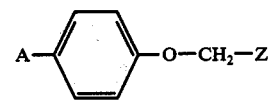

with a compound of the formula H$_2$N—X wherein X has the meanings indicated above and Z represents

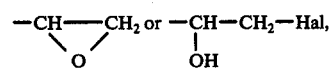

and Hal denotes halogen; (C) reacting a phenol of the formula

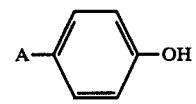

with a compound of the formula Z—CH$_2$NH—X wherein X has the meanings indicated above and Z denotes

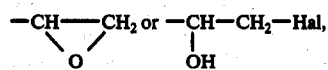

wherein Hal represents a halogen atom; and that the resulting compound is optionally reacted with an aldehyde of the formula $R_4$—CHO, wherein $R_4$ denotes hydrogen or a lower alkyl radical having up to 4 C atoms, to form an oxyzolidine of the formula

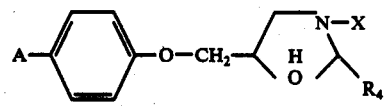

or is optionally reacted with an acid to form an acid addition salt.

12 Claims, No Drawings

DERIVATIVES OF 1-PHENOXY-3-AMINO-PROPAN-2-OL

This is a continuation-in-part application of U.S. Pat. application Ser. No. 531,344, filed Dec. 10, 1974.

The invention relates to new, pharmacologically valuable derivatives of 1-phenoxy-3-aminopropan-2ol of the general formula I

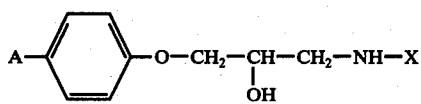

wherein X denotes

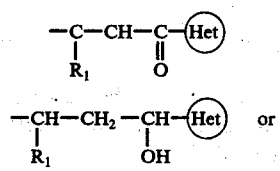

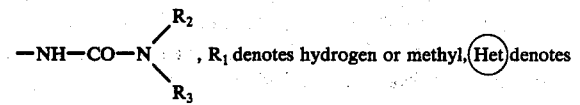

A denotes -CH$_2$-alkoxy, -O-alkoxyalkyl, -O-hydroxyalkyl or

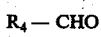, R$_1$ denotes hydrogen or methyl, (Het) denotes an aromatic or quasi-aromatic, 5-membered or 6-membered, monocyclic ring which is linked through a C atom which has one or 2 nitrogen, oxygen and/or sulphur hetero-atoms and which can be substituted additionally by one or more methyl groups, and R$_2$ and R$_3$ denote hydrogen, alkyl, alkenyl or cycloalkyl or, conjointly with the N atom to which they are linked, and optionally with a further oxygen or sulphur heteroatom, denote a saturated, 5-membered or 6-membered, monocyclic, heterocyclic structure, and alkyl radicals contain 1 to 4 carbon atoms, alkoxy radicals contain 1 to 4 carbon atoms, alkenyl radicals contain 3 or 4 carbon atoms and cycloalkyl radicals contain 5 to 7 carbon atoms.

The invention also emcompasses the acid addition salts and aldehyde condensation products of the compounds according to the invention, of the general formula I.

Products according to the invention which are preferred are those in which X has the meaning of

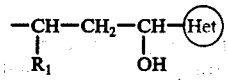

By the compounds of the general formula I, there are also understood, within the scope of the present invention, possible stereoisomers and optically active compounds and mixtures thereof, particularly the racemate.

Preferred substituents under the definition (Het) are radicals of pyrrole, pyrazole, imidazole, furane, thiophene, thiazole, pyridine, pyridazine, pyrimidine and parazine. These radicals can be additionally substituted with one or more methyl groups, preferably one, two or three methyl groups.

If the substituents R$_2$ and R$_3$, conjointly with the nitrogen atom to which they are linked, and optionally with an additional oxygen or sulphur hetero-atom, form a saturated, 5-membered of 6-membered, monocyclic, heterocyclic structure, they are to be understood particularly as the radicals of pyrrolidine, piperidine, morpholine and thiomorpholine.

The aldehyde condensation products of compounds of the general formula I are oxazolidines of the formula II

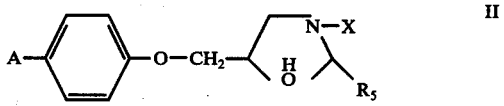

which are formed in the condensation of compounds of the general formula I with an aldehyde of the formula $$R_4 - CHO$$

in which R$_4$ represents hydrogen or a lower alkyl radical having up to 4 C atoms.

Inorganic and organic acids are suitable for the formation of salts with the compounds of the general formula I. Examples of suitable acids are hydrogen chloride, hydrogen bromide, phosphoric acid, sulphuric acid, oxalic acid, lactic acid, tartaric acid, acetic acid, salicylic acid, benzoic acid, citric acid, adipic acid or naphthalene-1,5-disulphonic acid. Pharmaceutically acceptable acid addition salts are preferred.

In order to prepare the compounds of the general formula I, a 1-phenoxy-3-aminopropan-2-ol of the general formula III is reacted with a compound of the general formula IV with elimination of H-Y to form a compound I according to the invention:

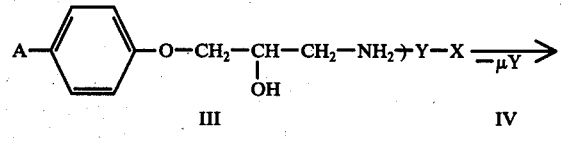

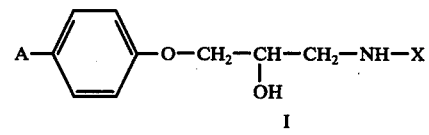

In this, X has the meaning already mentioned and Y denotes halogen, particularly chlorine or bromine, and, if X represents

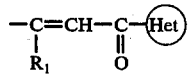

also —OH, —OK or —ONa.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, for example acetone or methyl ethyl keton; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example, alcohols. Examples of suitable alcohols are methanol, ethanol, isopropanol, tert.-butanol and the like. The reaction is carried out at temperatures from 20° C up to the reflux temperature of the solvent or dispersing agent used. The reaction frequently takes place even at normal temperature.

If X represents

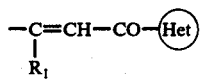

the reaction is accelerated by adding an acid, preferably hydrogen chloride. Examples of other suitable acids are carboxylic acids, such as, for example, formic acid, acetic acid, propionic acid and butyric acid; sulphonic acids, such as, for example, benzenesulphonic acid and p-toluenesulphonic acid; and mineral acids, such as, for example, sulphuric acid and phosphoric acid. If a compound of the general formula IV having Y = OH is employed, even catalytic amounts of the acid, for example of acetic acid or formic acid, are adequate to accelerate the reaction. If compounds of the general formula IV having Y = ONa or OK are employed, about 1 mol of the acid is added. Instead of adding an acid, it is also possible to accelerate the reaction by employing the compound of the general formula III in the form of a salt, for example the hydrohalide. If a compound of the general formula IV in which Y represents halogen is employed, it is also possible to employ this compound of the general formula IV in the form of the hydrohalide. In the preparative process according to the invention, the acid addition salts of the compound I can be formed, or, on adding an acid-binding agent such as potassium carbonate or sodium carbonate, the free amines can be formed.

Depending on the meaning of X, the starting compounds of the general formula IV which are required are either derivatives of the propen-1-one of the general formula V or of the propan-1-ol of the general formula VI:

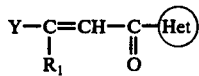

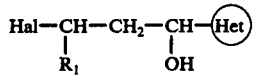

In these, Y has the meaning already indicated and Hal represents halogen, particularly chlorine or bromine. Starting compounds of the general formula V in which $R_1$ denotes methyl, and which therefore have the general formula Va

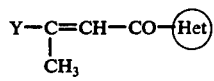

can be obtained either by reacting an ester of a heterocyclic carboxylic acid of the general formula VIIa, particularly a methyl or ethyl ester, with acetone under the conditions of an alkaline ester condensation, or by reacting an acetic acid ester, particularly methyl or ethyl acetate, under analogous conditions with a methyl ketone of the general formula VIIb. This gives the sodium salt or potassium salt of the formula VII or VIII, respectively:

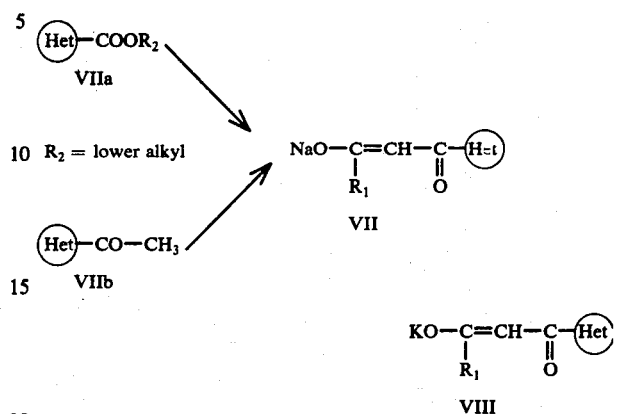

Starting compounds of the general formula V in which $R_1$ denotes hydrogen, and which therefore have the general formula Vb $$Y-CH=CH-CO-\text{(Het)} \qquad Vb$$

can be obtained by reacting a methyl ketone of the general formula VIIb, under the conditions of an alkaline ester condensation, with a formic acid ester, particularly methyl formate or ethyl formate.

This gives the sodium salt or potassium salt of the formula VII or VIII respectively, in which $R_1$ denotes hydrogen.

The free vinyl alcohols of the formula IX, which are tautomeric with the corresponding ketone derivatives of the formula X:

$$HO-C=CH-C-\text{(Het)} \rightleftarrows R_1-C-CH_2-C-\text{(Het)}$$
$$\;\;\;\;\;|\;\;\;\;\;\;\;\;\;\|\;\;\;\;\;\;\;\;\;\;\;\;\;\;\;\;\;\;\|\;\;\;\;\;\;\;\;\;\;\|$$
$$\;\;\;\;R_1\;\;\;\;\;\;O\;\;\;\;\;\;\;\;\;\;\;\;\;\;\;\;\;\;\;\;\;\;O\;\;\;\;\;\;\;\;O$$
$$\;\;\;\;\;\;\;\;\;\;IX\;\;\;\;\;\;\;\;\;\;\;\;\;\;\;\;\;\;\;\;\;\;\;\;\;X$$

are obtained from these salts by hydrolysis.

By reacting the compounds of the formula IX or X with suitable halogenating agents, such as, for example, thionyl chloride or phosphorus tribromide, the corresponding 3-halogeno-prop-2-en-1-ones of the general formula XI $$Hal-C=CH-CO-\text{(Het)}$$
$$\;\;\;\;\;\;|$$
$$\;\;\;\;\;R_1$$

wherein Hal represents halogen, particularly chlorine or bromine, are obtained. Compounds of the general formula VI can be prepared from the corresponding compounds of the formula XI by hydrogenation, appropriately by means of complex hydrides, such as, for example, lithium aluminium hydride, sodium borohydride or the like.

The compounds of the general formula III which are required as starting compounds can be prepared by reacting, with ammonia or with compounds which split off ammonia, a compound of the general formula XII or XIII,

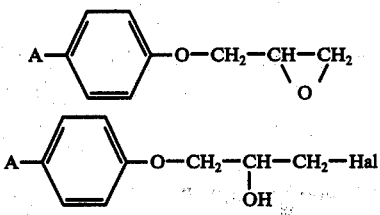

XII

XIII

Hal in XIII denoting a halogen atom, particularly chlorine or bromine, or a mixture of a compound XII with a compound XIII which is identically substituted in the phenyl nucleus. The reaction can be carried out under atmospheric pressure or under elevated pressure at ambient temperature and can be accelerated or brought to completion by supplying heat, for example by heating to 70° C.

The compounds of the general formulae XII and XIII can be prepared by reacting a phenol of the general formula XIV

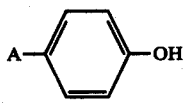

XIV with an epihalogenohydrin, appropriately with epichlorohydrin or epibromohydrin. A compound of the general formula XII or XIII or a mixture of compounds of the general formulae XII and XIII is formed in the course thereof, depending on the reaction conditions. The reaction product formed can be isolated before being further reacted with ammonia, but it can also be directly reacted further without isolation.

Compounds of the general formula I can also be prepared by reacting a compound of the general formula XV with a compound of the general formula XVI:

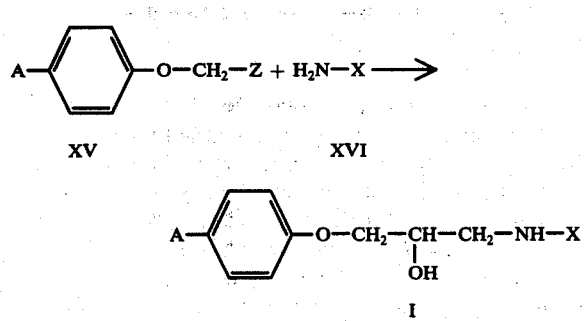

XV     XVI

I

In this, X has the meaning already mentioned and Z denotes:

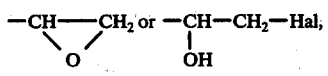

wherein Hal represents a halogen atom, particularly chlorine or bromine.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example, alcohols. Examples of suitable alcohols are methanol, ethanol, isopropanol, tert.-butanol and the like. The reaction is carried out at temperatures from 20° C up to the reflux temperature of the solvent or dispersing agent used. The reaction frequently takes place at temperatures of 40° to 50° C.

It can be advisable to employ the starting compound of the general formula XVI in a one- to 10-fold molar excess and/or to add the reaction component of the general formula XV in a dissolved or suspended form to the dissolved or suspended reaction component of the general formula XVI. The molar ratio between the compounds of the general formulae XV and XVI can be 1 : 1 to 1 : 10 and optionally even more.

In carrying out the reaction, a compound of the general formula XII or of the general formula XIII or a mixture of both these compounds, can be employed as the compound of the general formula XV.

If a compound of the general formula XIII is present, it is also possible to carry out the reaction in the presence of acid-binding agents, such as potassium carbonate, sodium carbonate and the like. Without an acid-binding agent, the hydrohalides of the compounds of the general formula I are then usually obtained.

The preparation of the starting compounds of the general formula XVI is described in the Examples.

In order to prepare the compounds of the general formula I it is also possible to react a phenol of the general formula XIV with a compound of the general formula XVII to give a compound of the general formula I:

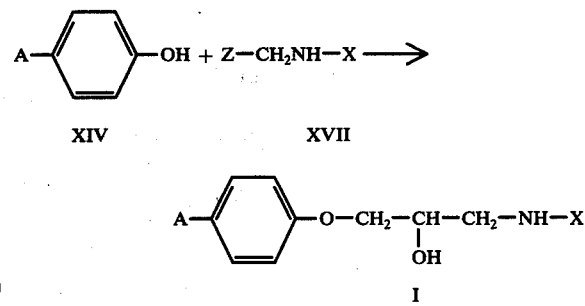

XIV     XVII

I

In this, X has the meaning already mentioned and Z denotes:

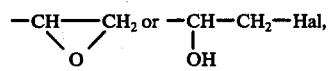

wherein Hal represents a halogen atom, particularly chlorine or bromine.

This reaction too is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, such as, for example, acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. Polar solvents, in particular, such as, for example, alcohols, are used as the solvent. Examples of suitable alcohols are methanol, ethanol, isopropanol, tert.-butanol and the like. If Z denotes

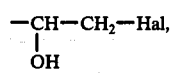

the reaction is generally carried out in the presence of an acid-binding agent, such as, for example, potassium carbonate, sodium carbonate or sodium bicarbonate. The reaction can also be carried out in aqueous alkalis, such as, for example, dilute sodium hydroxide or potassium hydroxide solution. The reaction temperature can be from 20° up to the reflux temperature of the solvent or dispersing agent used.

It can be advisable to employ the starting compound of the general formula XVII in a one- to 10-fold molar excess and/or to add the reaction component of the general formula XIV in a dissolved or suspended form to the dissolved or suspended reaction component of the general formula XVII. The molar ratio between the compounds of the general formula XIV and XVII can be 1:1 to 1:10 and optionally even more.

In carrying out the reaction it is possible to employ a compound of the general formula XVIII or of the general formula XIX or a mixture of both these compounds, as the compound of the general formula XVII.

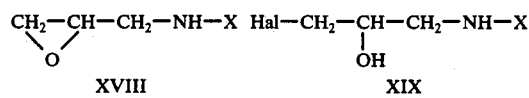

The compounds of the general formula XVIII and XIX can be prepared by reacting compounds of the general formula XVI with an epihalogenohydrin, appropriately with epichlorohydrin or epibromohydrin. Compounds of the general formula XVIII or XIX or a mixture of compounds of the general formula XVIII and XIX are formed in the course thereof, depending on the reaction conditions. The reaction product formed can be isolated in order to be reacted further, but it can also be directly reacted further without isolation.

The compounds of the general formula I in which X denotes the radical

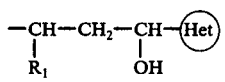

and which therefore have the general formula XX

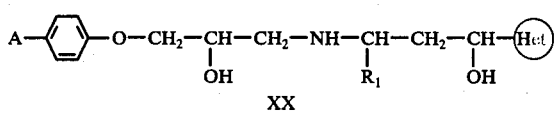

can also be prepared by hydrogenating a compound of the general formula XXI, XXII or XXIII

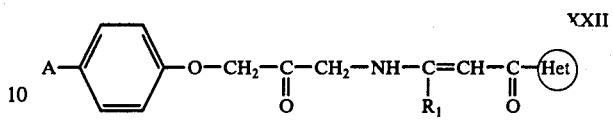

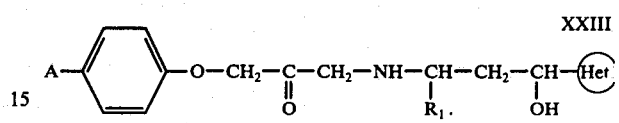

The compounds of the general formula I in which X denotes the radical

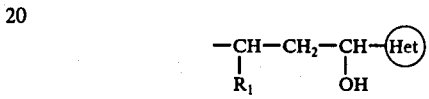

and $R_1$ represents hydrogen, and which therefore have the general formula

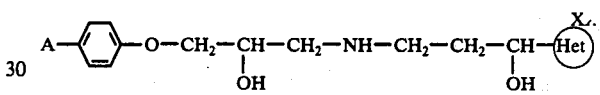

can, in addition, also be prepared by hydrogenating compounds of the general formula XXIIIa or XXIIIb

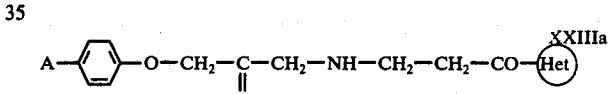

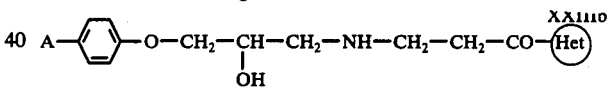

It is advantageous to employ, for the hydrogenation, complex hydrides, such as, for example lithium aluminium hydride, sodium borohydride and the like. The reaction is carried out under the reaction conditions which are known for these hydrides, normally in alcohol or an alcohol/water mixture at room temperature or elevated temperature, for example while boiling under reflux. In some cases the hydrogenation can also be carried out catalytically, for example using a palladium-charcoal catalyst.

The starting compounds of the general formula XXI are compounds according to the invention, of the general formula I, wherein X represents the radical

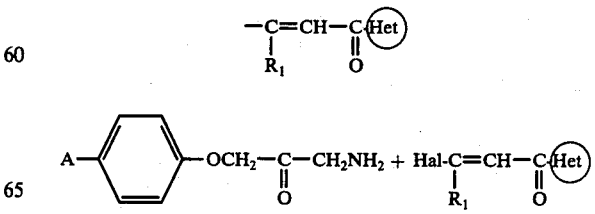

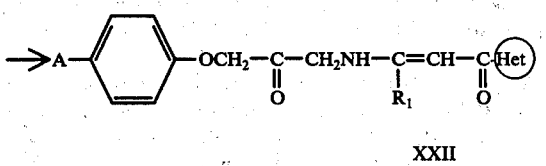

XXII

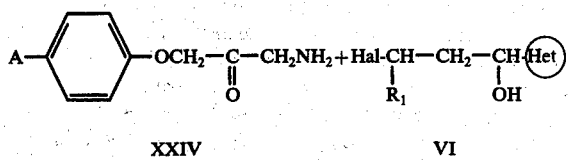

XXIV            VI

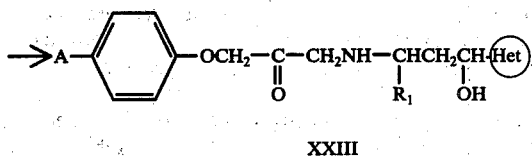

XXIII

The reaction between the compounds of the general formula XXIV and XI or XXIV and VI, respectively, is carried out in solvents such as benzene, toluene, chloroform, methylene chloride, dioxane and the like, at normal temperature or elevated temperature in the presence of at least molar quantities of acid-binding agents, such as potassium carbonate or sodium carbonate, or in the absence of acid-binding agents, the hydrohalides of the compounds XXII or XXIII being usually obtained in the latter case.

Compounds of the general formula XXIV can be prepared, for example, by gentle oxidation of compounds of the general formula III

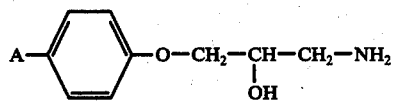

III

Starting compounds of the general formula XXIIIa can be prepared by a Mannich reaction from a compound of the general formula XXIV, formaldehyde and a methyl ketone of the general formula VIIb.

Compounds of the general formula XXIIIb can be prepared by a Mannich reaction from a compound of the general formula III, formaldehyde and a methyl ketone of the general formula VIIb.

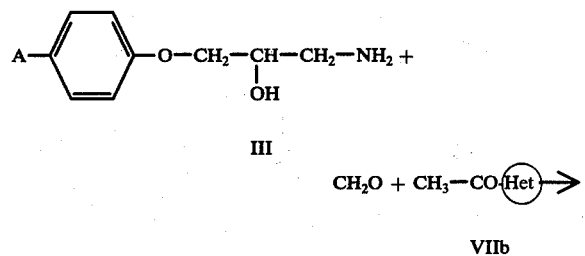

III $CH_2O + CH_3-CO-(Het) \rightarrow$

VIIb

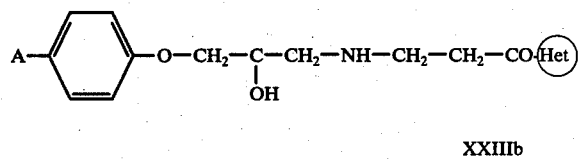

XXIIIb

Aldehyde condensation products of the formula II are obtained by reacting, in a diluent or solvent, for example ethanol, preferably in the presence of an acid catalyst, for example acetic acid or hydrochloric acid, and preferably at elevated temperature, compounds of the general formula I with an aldehyde of the formula $R_3$—CHO wherein $R_3$ denotes hydrogen or a lower alkyl radical. The water formed in the reaction can be removed by azeotropic distillation with the aid of an entraining agent, for example benzene, or by means of a dehydrating agent, such as anhydrous potassium carbonate.

The acid addition salts of the compounds of the general formula I can be prepared from the components in a manner which is in itself known. The use of a diluent is generally advantageous here, the di-salts of the compounds of the general formula I being generally obtained when there is an excess of acid. The mono-acid addition salts are obtained either by controlled addition of only 1 mol of acid or by partial hydrolysis of the di-acid addition salts.

The compounds of the general formula I, their aldehyde condensation products II and their pharmaceutically acceptable acid addition salts possess valuable pharmaceutical properties. Thus they are suitable, for example, for the treatment or prophylaxis of heart diseases. In addition, some of them have very marked β-adrenalytic or anti-arrhythmic properties. The compounds can, therefore, be used as pharmaceutical preparations, on their own, in mixtures with one another or mixed with diluents or excipients which are pharmaceutically unobjectionable. The pharmaceutical preparations can be present in the form of, for example, tablets, capsules, aqueous or oily solutions or suspensions, emulsions, injectable aqueous or oily solutions or suspensions, dispersible powders or aerosol mixtures. Besides the compounds of the general formula I, the pharmaceutical preparations can also contain one or more other pharmaceutically active substances, for example sedatives, such as, for example, Luminal, Meprobamat and Chlorpromazine; vasodilators, such as, for example, glycerol trinitrate and carbochromene; diuretics, such as, for example, chlorothiazide; agents for tonicising the heart, such as, for example, digitalis preparations; hypotension agents, such as, for example, Rauwolfia alkaloids; and broncho-dilators and sympathomimetic agents, such as, for example, Isoprenalin and Ephedrin.

Compounds according to the invention, of the general formula I, which are particularly preferred are those in which X has the meaning:

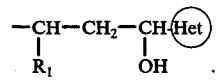

The blocking action of the compounds according to the invention on the β1-receptors of the heart and on the β2-receptors of the cardiovascular system was investigated as follows: the blood pressure in the left-hand ventricle was measured on mongrel dogs of both sexes under an anaesthesia by Chloralose-urethane-morphine and the pressure signal was continuously differentiated by means of an analogue computer (BRUSH Instruments, Cleveland/Ohio) and, inter alia, the rate of pressure increase (Dp/dt) was recorded. In addition, the perfusion of a femoral artery was measured by means of an electromagnetic flow-meter (Model M4000 of Messrs. Statham) and the perfusion was recorded in ml/minute.

Alterations in the maximum rate of pressure increase (Dp/dt max.) compared with the zero value were induced by intravenous administration of Isoproterenol (0.5 gamma/kg), a known sympathomimetic agent (β1-reaction), while alterations of the peripheral perfusion, compared with the zero value, were induced by intraarterial administration of Isoproterenol (0.05 gamma/kg) (β2-reaction) (D. DUNLOP and R. G. Shanks: Selective blockade of adrenoceptive beta-receptors in the heart. Brit. J. Pharmac. Chemother. (1968) 32, 201–218).

The substances to be tested for β-receptor blocking were administered intravenously in increasing dosages to the animals which had been anaesthetised and stimulated by means of Isoproterenol, and the quantity of substance was determined at which a 50% inhibition of the two reactions caused by Isoproterenol occurred (ED50). The ED50 values of the β1-receptor inhibition (mg/kg intravenous) and the ED50 values of the β2-receptor inhibition (mg/kg intravenous) are given in the table which follows. In addition, the relative ED 50 values were calculated for both cases, taking as a basis 4-(2-hydroxy-3-isopropylamino-propoxy)-acetanilide, which was employed as a reference substance, the ED 50 values of the latter being made equivalent to 100. The quotient derived from the ED 50 of the β2-receptor inhibition and the ED 50 of the β1-receptor inhibition represents a measure of the cardioselective action of the substances under investigation. The higher this quotient is, the better the cardioselective action. If the quotient of the reference substance 4-(2-hydroxy-3-isopropylamino-propoxy)-acetanilide is made equivalent to 1, the relative factor indicates how much better the cardioselective action of the compound according to the invention is than the reference substance.

Furthermore, the relative ED 50 values of the β1-receptor inhibition (column 2 of the table which follows) are a measure of the effectiveness of the substances to be tested. The lower the figures are, the more active the substances, that is to say the smaller the quantity required for the production of the therapeutic effect.

4-(2-Hydroxy-3-isopropylamino-propoxy)-acetanilide, which is employed as the reference substance, is a preparation which is commercially available as β-blocker and which carries the international unprotected trade name "Practolol."

| Substance under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient: ED 50 β2-receptor inhibition / ED 50 β1-receptor inhibition | quotient, on basis of reference substance = 1 |
|---|---|---|---|---|---|---|
| 1-(-p-[2-Hydroxy-ethoxy]-henoxy)-3-(1-[2-methyl-pyridyl-5]-1-hydroxy-butyl(3)-amino)-propan-2-ol | 0.073 | 30.7 | 8.14 | 30.7 | 112 | 1 |
| 1-(p-Methoxybutoxy-phenoxy)-3-(1-[2,4-dimethyl-pyrimidyl-5]-hydroxy-butyl(3)-amino)-propan-2-ol | 0.089 | 37.4 | 15.99 | 58.8 | 176 | 1.6 |
| 1-(p-Ethylureido-phenoxy)-3-(1-[2,4-dimethyl-pyrimidyl-5-]-1-hydroxy-butyl(3)-amino)-propan-2-ol | 0.093 | 39.1 | 12.79 | 48.3 | 137 | 1.2 |
| 1-(p-Allylureido-phenoxy)-3-(1-[2,4-dimethyl-pyrimidyl-5]-1-hydroxy-butyl(3)-amino)-propan-2-ol | 0.019 | 7.9 | — | — | | |
| 1-(p-Isopropylureido-phenoxy)-3-(1-[2,4-dimethyl-pyrimidyl-5]-1-hydroxy-butyl(3)-amino)-propan-2-ol | 0.022 | 9.2 | 2.71 | 10.2 | 124 | 1.1 |
| 1-(p-Cyclohexylureido-phenoxy)-3-(1-[pyridyl-3]-1-hydroxy-butyl(3)-amino)-propan-2-ol | 0.003 | 1.3 | 1.02 | 3.8 | 409 | 2.9 |
| 1-(p-[2-n-Propoxy-ethoxy]-phenoxy)-3-(1-[2-methyl-pyridyl-5]-1-hydroxy-butyl(3)-amino)-propan-2-ol | 0.035 | 14.7 | 5.1 | 19.2 | 146 | 1.3 |
| 1-(p-Cyclohexylureido-phenoxy)-3-(1-[2,4-dimethyl-pyrimidyl-5]-1-hydroxy-butyl(3)-amino)-propan-2-ol (as L-(+)-tartrate) | 0.011 | 4.6 | 1.38 | 5.2 | 128 | 1.1 |
| 1-(p-Cyclohexylureido-phenoxy)-3-(1-[2-methyl-pyridyl-5]-1-hydroxy-butyl(3)-amino)-propan-2-ol | 0.006 | 2.5 | 1.57 | 5.9 | 245 | 2.4 |
| 1-(p-Ethoxymethylene-phenoxy)-3-(1-[2,4-dimethyl-pyrimidyl-5]-1-hydroxy-butyl(3)-amino)-propan-2-ol (as L-(+)-tartrate | 0.019 | 7.9 | 2.88 | 10.7 | 144 | 1.4 |
| 1-(p-Ethoxymethylene-phenoxy)-3-(1-[pyridyl-3]-1-hydroxy-butyl(3)-amino)-propan-2-ol | 0.010 | 4.2 | — | — | | |
| 1-(p-Ethylureido-phenoxy)-3-(1-[pyridyl-3]-1-hydroxy-butyl(3)-amino)- | | | | | | |

| Substance under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient: ED 50 β2-receptor inhibition / ED 50 β1-receptor inhibition | quotient, on basis of reference substance = 1 |
| --- | --- | --- | --- | --- | --- | --- |
| propan-2-ol | 0.013 | 5.5 | — | | — | |
| 1-(p-Ethoxyethoxy-phenoxy)-3-(1-[pyridyl-3]-1-hydroxy-butyl(3)-amino)-propan-2-ol | 0.009 | 3.8 | 2.76 | 10.1 | 296 | 2.7 |
| Reference substance: | | | | | | |
| 4-(2-Hydroxy-3-isopropyl-amino-propoxy)acetanilide | 0.238 | 100 | 26.505 | 100 | 110 | 1 |

The isoproterenol-induced increase in heart rate in anaesthetized animals represents mainly the response of the cardiac β1-receptors. The dose of the antagonists (mg/kg i.v.) which inhibits this response of isoproterenol (0.5 gamma/animal) in guinea pigs, anaesthetized with urethane, by 50% : ED-50 was determined.

The isoproterenol-induced relaxation of contracted isolated tracheal chain of guinea pigs represents the response of the tracheal β2-receptors. The bath concentrations of the antagonists which reduce the isoproterenol effects by 50% were determined: ED-50 : g/ml bath.

The following Table demonstrates the results obtained by the beforementioned methods: The ratio between the β2 and β1 response is 1 for the reference compound and 2.3 for one of the substances of the present invention, indicating a preference of the compound of the present invention to β1-receptors being 2.3 times greater than the reference compound, in other words, the investigational drug has a cardiac selectively index being 2.3 times better than the reference compound. Similar results are obtained with other substances of the present invention.

A tablet containing a compound according to the invention and having a total weight of 100 mg, can have the following composition, for example:
- 5 mg of 1-(p-allylureidophenoxy)-3-(1-[2,4-dimethyl-pyrimidyl-5]-1-hydroxybutyl(3)-amino)-propan-2-ol
- 10 mg of colloidal silicic acid (Aerosil)
- 72.5 mg of DAB7 lactose
- 1.5 mg of gelatine
- 8.5 mg of DAB7 maize starch and
- 2.5 mg of Mg stearate USPXVIII Depending on the severity of the case to be treated, it is possible, for example, to administer 1 to 2 of these tablets to a patient three times daily.

The preparation of the compounds of the general formula I is illustrated in greater detail in the following examples. The compounds are frequently oils which cannot be distilled, so that in some cases no melting point is shown. However, in all cases the structure indicated has been checked by molecular analysis and/or the infrared spectrum or nuclear resonance spectrum.

EXAMPLE 1

5.1 g of 1-(p-methoxybutoxyphenoxy)-3-aminopropan-2-ol

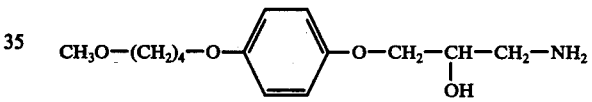

are dissolved in 50 ml of ethanol, 3.3 g of nicotinoylacetone

| Substance under investigation | β1-receptor inhibition parameter: heart rate response to isoproterenol : ED-50 mg/kg i.v. | Relative β1-receptor inhibition (reference substance = 100) | β2-receptor inhibition parameter: isolated tracheal chain : ED-50 g/ml bath | Relative β2-receptor inhibition (reference substance = 100) | Ratio: ED-50 β2-receptor inhibition / ED-50 β1-receptor inhibition on basis of reference substance = 1 |
| --- | --- | --- | --- | --- | --- |
| 1-(p-[2-n-Propoxy-ethoxy]-phenoxy)-3-(1-[2-methyl-pyridyl-5]-1-hydroxy-butyl(3)-amino)-propan-2-ol | 0.177 | 3.39 | $3.10^{-6}$ | 7.7 | 2.3 |
| Reference substance | | | | | |
| 4-(2-Hydroxy-3-isopropyl-amino-propoxy)-acetanilide | 5.3 | 100 | $3.9.10^{-5}$ | 100 | 1 |

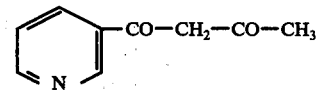

are then added and, after adding 1 drop of formic acid, the solution is heated under reflux for 3 hours. The solution is then concentrated in vacuo. A solid residue remains, which is recrystallised from toluene.

This gives 1-(2-nicotinoyl-1-methylvinylamino)-3-(p-methoxybutoxyphenoxy)-propan-2-ol of the formula

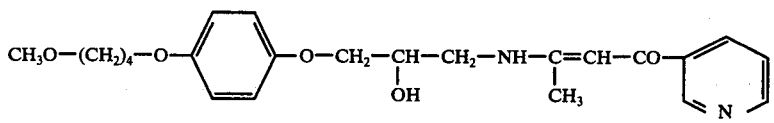

Melting point: 108° C Analysis: ($C_{23}H_{30}N_2O_5$) calculated: C 66.7 H 7.2 N 6.8 found: 66.6 7.2 7.0 Yield: 78% of theory.

The nicotinoyl-acetone required can be prepared either from nicotinic acid ethyl ester and anhydrous acetone in the presence of sodium ethylate in a known manner, for example following A. Ferenczy, Monatshefte fur Chemie page 674 (1897), or from acetylpyridine in accordance with the following instructions:

22.4 g of potassium tert.-butylate are suspended in 150 ml of anhydrous benzene, a mixture of 18.3 g of ethyl acetate and 24.2 g of 3-acetylpyridine is then added dropwise slowly, with stirring at 10° C, and the mixture is then allowed to stand at room temperature for 24 hours. The product is then filtered off and washed twice with anhydrous benzene, then twice with anhydrous ethanol and finally twice with diethyl ether. This gives the potassium salt of nicotinoyl-acetone in a yield of 77% of theory. The free nicotinoyl-acetone can be obtained practically quantitatively from the potassium salt by acid hydrolysis.

The 1-(p-methoxybutoxyphenoxy)-3-amino-propan-2-ol required can be prepared as follows:

4-(4-Methoxybutoxy)-phenyl benzyl ether

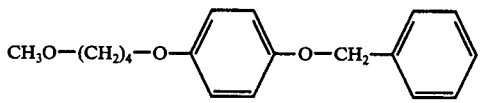

Melting point: 60°-61°
is obtained in the usual manner (heating with acetone in the presence of excess potassium carbonate) from hydroquinone monobenzyl ether and (4-bromobutyl) methyl ether.

Hydrogenation of this in methanolic solution (Raney nickel, 50 atmospheres gauge of $H_2$, 50°) gives b 4-(4-methoxybutoxy)-phenol

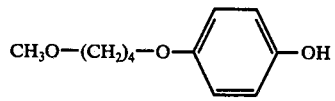

as an oil, boiling point 138°-143°/0.1 mm Hg.

This phenol can be reacted with epichlorohydrin in the usual manner; the crude 4-(4-methoxybutoxy)-phenyl glycidyl ether

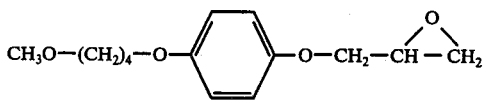

thus obtained is stirred, directly, with excess saturated aqueous-alcoholic ammonia solution for 20 hours at room temperature. The reaction mixture is evaporated under reduced pressure and the residue is distilled in vacuo; this gives, in a 57% yield, 1-(4-[4-methoxybutoxy]-phenoxy)-3-amino-propan-2-ol

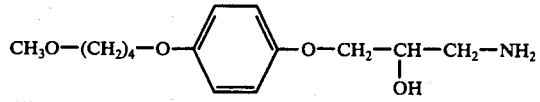

boiling point 207°-219°/0.1 mm Hg; melting point: 84°-88°. Melting point: 92°-93° after recrystallisation from toluene or reprecipitation from dilute hydrochloric acid.

If β-bromoethyl ethyl ether is used instead of (4-bromobutyl) methyl ether, 4-(2-ethoxyethoxy)-phenyl benzyl ether

melting point: 35°-37°
is obtained in an identical manner, and the following compounds are obtained from this in a corresponding manner, as indicated:

4-(2-ethoxyethoxy)-phenol

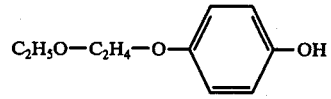

as an oil;
4-(2-ethoxyethoxy)-phenyl glycidyl ether

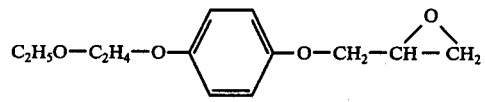

as a low-melting solid, boiling point 135°-143°/0.1 mm Hg, and 1-[4-(2-ethoxyethoxy)-phenoxy]-3-aminopropan-2-ol

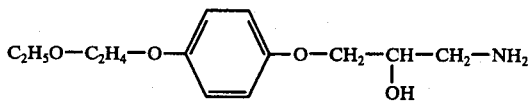

melting point: 84°-86°.

After condensation with nicotinoyl-acetone, as described initially, this gives 1-(2-nicotinoyl-1-methyl-vinylamino)-3-(p-ethoxyethoxy-phenoxy)-propan-2-ol, melting point 88°-89°.

EXAMPLE 1a 6.1 g of 1-(p-cyclohexylureido-phenoxy)-3-aminopropan-2-ol of the formula

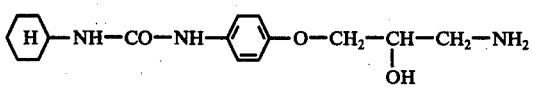

are dissolved in 50 ml of anhydrous toluene and 5.7 g of anhydrous potassium carbonate are added. A mixture of 4.4 g of 1-(β-pyridyl)-3-chloro-butan-1-ol hydrochloride of the formula

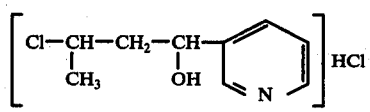

(prepared by reduction from 2-nicotinoyl-1-methylvinyl chloride hydrochloride described in Example 2) in 50 ml of anhydrous toluene is slowly added to the preceding mixture, whilst stirring and cooling, the whole is then heated for 18 hours whilst stirring, allowed to cool and filtered, the residue is dissolved in water and the solution is adjusted to pH 1 with 2 N hydrochloric acid. The acid solution is then washed three times with ethyl acetate, the pH is raised to 5, and the solution is again washed three times with ethyl acetate, then rendered alkaline to pH 9 with sodium carbonate solution and extracted three times with chloroform. The combined chloroform extracts are dried and concentrated in vacuo. 1-(p-Cyclohexylureidophenoxy)-3-(1-hydroxy-1-pyridyl-(3)-butyl3-amino)-propan-2-ol is thus obtained, as a colourless oil of the formula

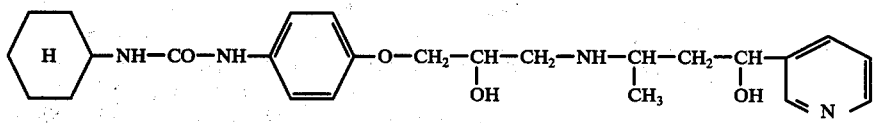

EXAMPLE 2

6.1 g of 1-(p-cyclohexyluredio-phenoxy)-3-aminopropan-2-ol

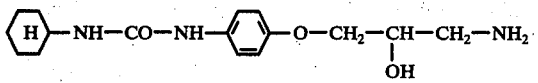

are dissolved in 50 ml of anhydrous toluene and 5.7 g of anhydrous potassium carbonate are added. A mixture of 4.4 g of 2-nicotinoyl-1-methylvinyl chloride hydrochloride of the formula

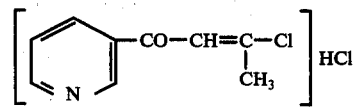

(prepared from the sodium salt of nicotinoyl-acetone, which is first converted by means of HCl gas into the hydrochloride of free nicotinoyl-acetone and then, using thionyl chloride, into nicotinoyl-methylvinyl chloride hydrochloride) in 50 ml of anhydrous toluene is added slowly, with cooling and stirring, to this mixture and stirring is subsequently continued for 36 hours at room temperature. The product is then filtered and the residue is dissolved in water and the solution is rendered alkaline by means of sodium carbonate and extracted three times with chloroform. The chloroform extracts are concentrated, together with the original toluene filtrate, in vacuo at approx. 14 to 20 mm Hg. 1-(2-Nicotinoyl-1-methylvinylamino)-3-(p-cyclohexylureidophenoxy)-propan-2-ol is thus obtained after repeated recrystallisation from aqueous ethanol.

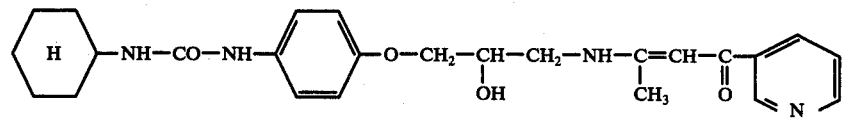

Melting point: 168° C Analysis: ($C_{25}H_{32}N_4O_4$) calculated: C 66.4 H 7.1 N 12.4 found: 66.5 6.9 12.3 Yield: 81% of theory.

EXAMPLE 3

6.2 g of 1-(2-nicotinoyl-1-methylvinylamino)-3-(p-methoxybutoxyphenoxy)-propan-2-ol

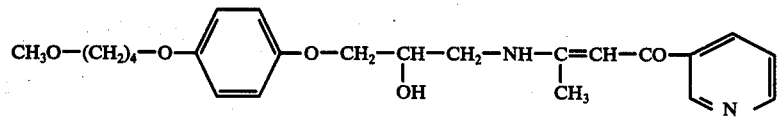

are dissolved in 65 ml of ethanol, the solution is heated under reflux and 2.8 g of sodium borohydride are added in portions at this temperature in the course of 40 minutes. The mixture is then allowed to boil under reflux for a further 11 hours. The solution is then concentrated in vacuo, the residue is dissolved in 40 ml of chloroform and 40 ml of water, the chloroform phase is separated off, the aqueous phase is extracted twice more with fresh chloroform and the combined chloroform phases are then concentrated in vacuo, after drying by means of sodium sulphate. An oil remains, which is dissolved in dilute aqueous hydrochloric acid. The hydrochloric acid solution is washed three times with ethyl acetate, then neutralised to pH 5 with aqueous sodium carbonate solution and again washed three times with ethyl acetate. The solution is then rendered alkaline, to pH 9, by means of sodium carbonate solution and extracted three times with chloroform. After washing with water and drying over sodium sulphate, the chloroform solution is concentrated in vacuo. The residual oil is then heated to 180° C in a vacuum of 0.1 mm Hg, a small amount of impurity being distilled off. The distillation residue is dissolved in absolute dioxane, treated with animal charcoal, filtered and concentrated in vacuo. This gives 1-(p-methoxybutoxyphenoxy)-3-(1-hydroxy-1-pyridyl-(3)-butyl-3-amino)-propan-2-ol as a colourless oil

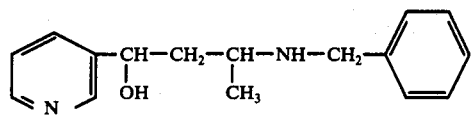

which can be debenzylated in the customary manner by means of hydrogen in an autoclave to give 1-(β-

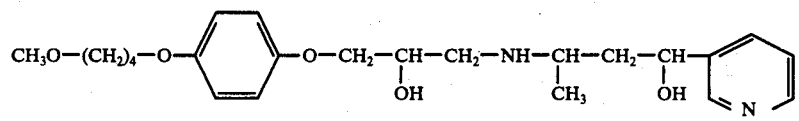

pyridyl)-3-aminobutan-1-ol (a viscous oil)

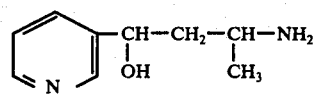

Analysis: ($C_{23}H_{34}N_2O_5$) calculated: C 66.0 H 8.1 N 6.7 found: 65.8 8.2 6.5 Yield: 63% of theory.

The same product is also obtained by reacting 1-(p-methoxybutoxyphenoxy)-2,3-epoxypropane

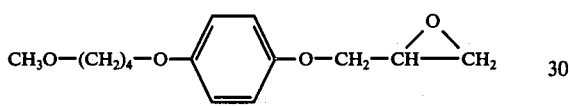

(prepared by heating 4-methoxybutoxyphenol with epichlorohydrin and potassium carbonate in anhydrous toluene) with 1-(β-pyridyl)-3-aminobutan-1-ol

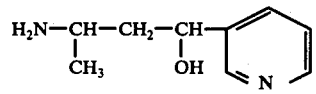

The 1-(β-pyridyl)-3-aminobutan-1-ol can be prepared as follows:

The potassium salt of nicotinoyl-acetone is first synthesised as indicated in Example 1. 2 g of the potassium salt of nicotinoyl-acetone are then suspended on 50 ml of ethanol and 1.6 g of benzylamine hydrochloride are added and the mixture is stirred at room temperature for 24 hours. The suspension is filtered and the residue is washed with ethanol. The filtrate, including the alcohol washings, is concentrated in vacuo. An oil remains, which becomes solid after a short time. The solidified oil, together with the residue left from the alcohol washings, is repeatedly triturated with water and is then recrystallised from ethanol. This gives N-(2-nicotinoyl-1-methylvinylamino)benzylamine, melting point 102°-104°, in 88% yield.

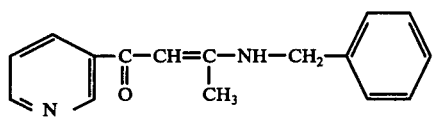

This gives, in a 62% yeild, by reduction using sodium borohydride analogously to the instructions for reduction in Example 3, 1-(β-pyridyl)-3-benzylaminobutan-1-ol (an oil)

1-(β-Pyridyl)-3-aminobutan-1-ol can also be prepared as follows:

5 g of 2-nicotinoyl-1-methylvinylamine

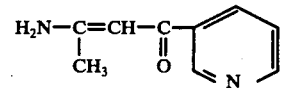

are dissolved in 50 ml of ethanol and a total of 6 g of sodium borohydride is added in portions over the course of 6 hours, at 70° C and with stirring. The mixture is then kept at 70° C for a further 10 hours. It is then concentrated, the residue is taken up in chloroform/water and the chloroform phase is separated off, dried and concentrated in vacuo (10 to 14 mm Hg). The residual oil is distilled. The fraction passing over between 125 and 150° C at 0.3 mm Hg is then dissolved in dioxane and the solution is treated with a solution of tartaric acid in dioxane. The slightly hygroscopic tartrate which is precipitated is filtered off, recrystallised from dimethylformamide/ethyl acetate and finally converted into the free base. This gives 1-(β-pyridyl)-3-aminobutan-1-ol in a 73% yield.

The 2-nicotinoyl-1-methylvinylamine required for the reduction can be prepared as follows:

7.5 g of nicotinoyl-acetone are dissolved in 45 ml of anhydrous ethanol and, after adding 20 ml of ammonia, the mixture is then stirred for 3 days at 50° C in an autoclave. Concentrating the clear solution leaves an oil which becomes solid after a short time. After recrystallisation from toluene, 2-nicotinoyl-1-methylvinylamine (melting point 82°) is obtained in a 91% yield.

EXAMPLE 4

2.6 g of 1-amino-3-(p-ethoxymethylenephenoxy)-propan-2-ol hydrochloride

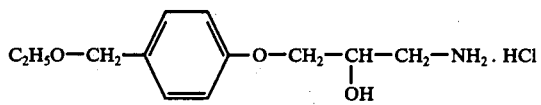

are suspended in 40 ml of ethanol, 1.8 g of the sodium salt of thenoyl-(2)-vinyl alcohol

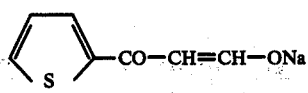

are then added and the mixture is stirred at room temperature for 24 hours. It is then filtered and the residue is washed with alcohol. The filtrate, including the alcohol washings, is concentrated in vacuo. An oil remains, which becomes solid after standing for a fairly long time and is recrystallised from dilute alcohol. This gives 1-(thenoyl-(2)-vinylamino)-3(p-ethoxymethylenephenoxy)-propan-2-ol of the formula

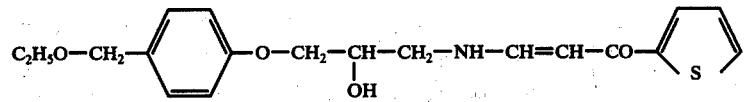

Melting point: 103° C Analysis: ($C_{19}H_{23}NO_4S$) calculated: C 63.1 H 6.4 N 3.9 found: 62.9 6.5 3.9 Yield: 91% of theory.

The sodium salt of thenoyl-(2)-vinyl alcohol which is required can be prepared as follows:

32 g of 2-acetylthiophene and 18 g of ethyl formate are added dropwise over the course of 20 minutes, with stirring, to a suspension of 1.3 g of sodium methylate in 100 ml of absolute ether at a temperature of 10° to 15° C. The mixture is then allowed to stand at room temperature for 29 hours. It is then filtered and the residue is washed with a little absolute alcohol and then with ether. This gives the sodium salt of thenoyl-(2)-vinyl alcohol in a 95% yield.

EXAMPLE 5

2.5 g of 1-(p-methoxymethylenephenoxy)-3-aminopropan-2-ol hydrochloride

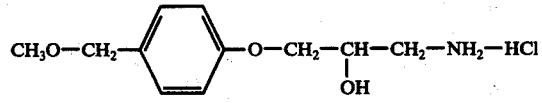

are suspended in 40 ml of ethanol, 1.6 g of the sodium salt of furoyl-(2)-vinyl alcohol

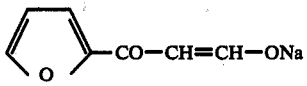

are then added and the mixture is stirred at room temperature for 24 hours. The mixture is then worked up as described in Example 4. This gives 1-(furoyl-(2)-vinylamino)-3-(p-methoxymethylenephenoxy)-propan-2-ol of the formula

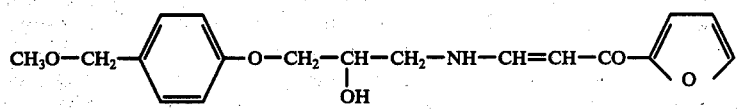

Melting point: 108° C Analysis: ($C_{18}N_{21}NO_5$) calculated: C 65.2 H 6.4 N 4.2 found: 65.4 6.5 4.0 Yield: 73% of theory.

The sodium salt of furoyl-(2)-vinyl alcohol which is required as the starting product can be prepared from 2-acetylfurane, ethyl acetate and sodium methylate, analogously to the instructions for preparing the sodium salt of thenoyl-(2)-vinyl alcohol, as described in Example 4.

EXAMPLE 6

54.0 g of 1-(p-[4-methoxybutoxy]-phenoxy)-3-aminopropan-2-ol

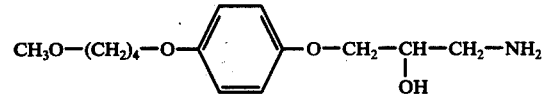

37.3 g of 6-methylnicotinoyl-acetone

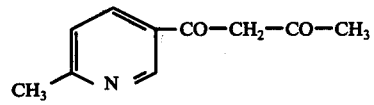

400 ml of ethanol and 0.1 ml of formic acid are heated to 50° for 1 hour and stirred at room temperature for a further 20 hours. Filtration gives 61.3 g of 1-(2-[6-methylnicotinoyl]-1-methylvinylamino)-3-(p-[4-methoxybutoxy]-phenoxy)-propan-2-ol

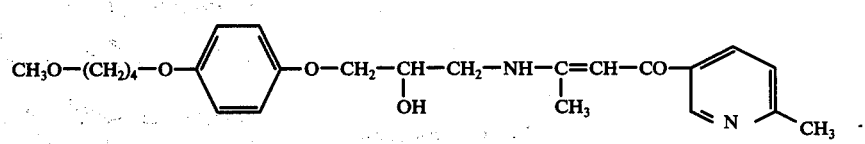

Melting point: 143°–145°. A further 15.0 g of the same substance can be obtained from the filtrate. Yield: 89% of theory.

19.0 g of this substance are dissolved at 70° in 200 ml of anhydrous ethanol. 6.0 g of sodium boranate are introduced in portions and the reaction mixture is heated at 70° for a further 7 hours and evaporated under reduced pressure. The residue is taken up in water and ethylene chloride and the clear ethylene chloride solution is thoroughly stirred with water and sufficient dilute sulphuric acid to make the pH value of the aqueous solution 6.5, and finally the latter is adjusted to pH 8. The base which is precipitated in this way as an oil is once more taken up in ethylene chloride and isolated in the usual manner. This gives 10.3 g of 1-(p-[4-methoxybutoxy]-phenoxy)-3-(1-[2-methylpyridyl-5]-1-hydroxybutyl-3-amino)-propan-2-ol

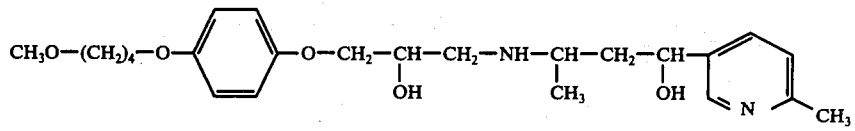

as a viscous oil; the neutral naphthalene-1,5-disulphonate (containing ½ mol of the disulphonic acid) forms white, hygroscopic crystals, melting point 145°–150° (decomposition).

Analysis: ($C_{24}H_{36}N_2O_5$) calculated: C 66.6 H 8.4 N 6.5 O 18.5 found: 66.4 8.4 6.3 18.8

The compounds listed in the following table were prepared in a manner corresponding to Examples 1–6.

| A | X | |
|---|---|---|
| cyclohexyl-NH—CO—NH— | —CH(CH₃)—CH₂—CH(OH)-pyridyl | Oil |
| $C_2H_5O-CH_2-$ | —C(CH₃)=CH—C(O)-pyridyl | Melting point: 64° C |
| $C_2H_5O-CH_2-$ | —CH(CH₃)—CH₂—CH(OH)-pyridyl | Oil |
| $C_2H_5-NH-CO-NH-$ | —C(CH₃)=CH—CO-pyridyl | Melting point: 143° C |
| $C_2H_5-NH-CO-NH-$ | —CH(CH₃)—CH₂—CH(OH)-pyridyl | Melting point: 50° C (decomposition) |
| $C_2H_5O-CH_2-$ | —CH₂—CH₂—CH(OH)-thienyl | Oil |
| $CH_3O-CH_2-$ | —CH₂—CH₂—CH(OH)-furyl | Oil |
| $CH_3O-(CH_2)_4-O-$ | —C(CH₃)=CH—CO-(2,6-dimethylpyridyl) | Melting point: 79–81° C |
| $CH_3O-(CH_2)_4-O-$ | —CH(CH₃)=CH₂—CH(OH)-(2,6-dimethylpyridyl) | Oil |
| cyclohexyl-NH—CO—NH— | —C(CH₃)=CH—CO-(2,6-dimethylpyridyl) | Melting point: 179–180° C |
| cyclohexyl-NH—CO—NH— | —CH(CH₃)—CH₂—CH(OH)-(2,6-dimethylpyridyl) | Oil; salt containing ½ mol L-(+)-tartaric acid: melting point: 113–118° (decomposition) |

-continued
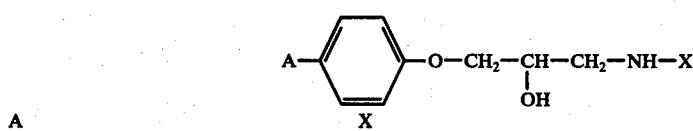
| A | X | |
|---|---|---|
| $C_2H_5O-CH_2-$ | 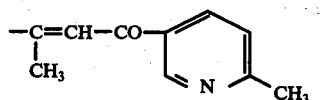 | Melting point: 133-134° |
| $C_2H_5O-CH_2-$ | 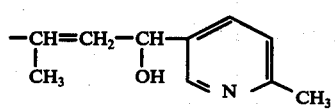 | Oil |
| $C_2H_5-NH-CO-NH-$ | 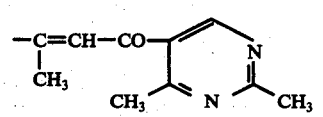 | Melting point: 155-157° |
| $C_2H_5-NH-CO-NH-$ | | Oil |
| $C_2H_5O-CH_2-$ | 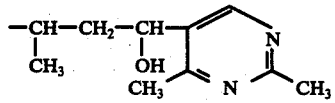 | Melting point: 105-106° |
| $C_2H_5O-CH_2-$ | 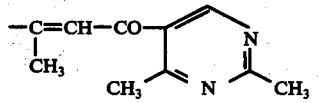 | Oil; salt with ½ mol L-(+)-tartaric acid: melting point: 69-70°, hygroscopic |
| 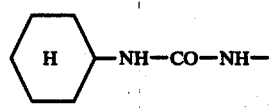 | 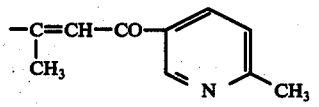 | Melting point: 188-189° |
| 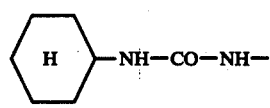 | 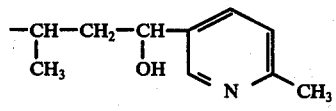 | Melting point: 102-105° |
| $HO-C_2H_4-O-$ | 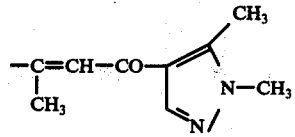 | Melting point: 151-152° |
| $HO-C_2H_4-O-$ | 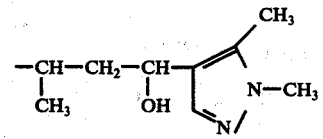 | Oil |
| $C_2H_5-NH-CO-NH-$ | 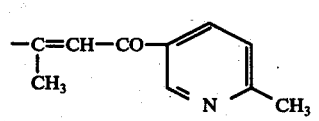 | Melting point: 157-159° |
| $C_2H_5-NH-CO-NH-$ | 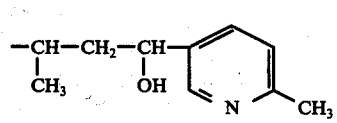 | Oil |

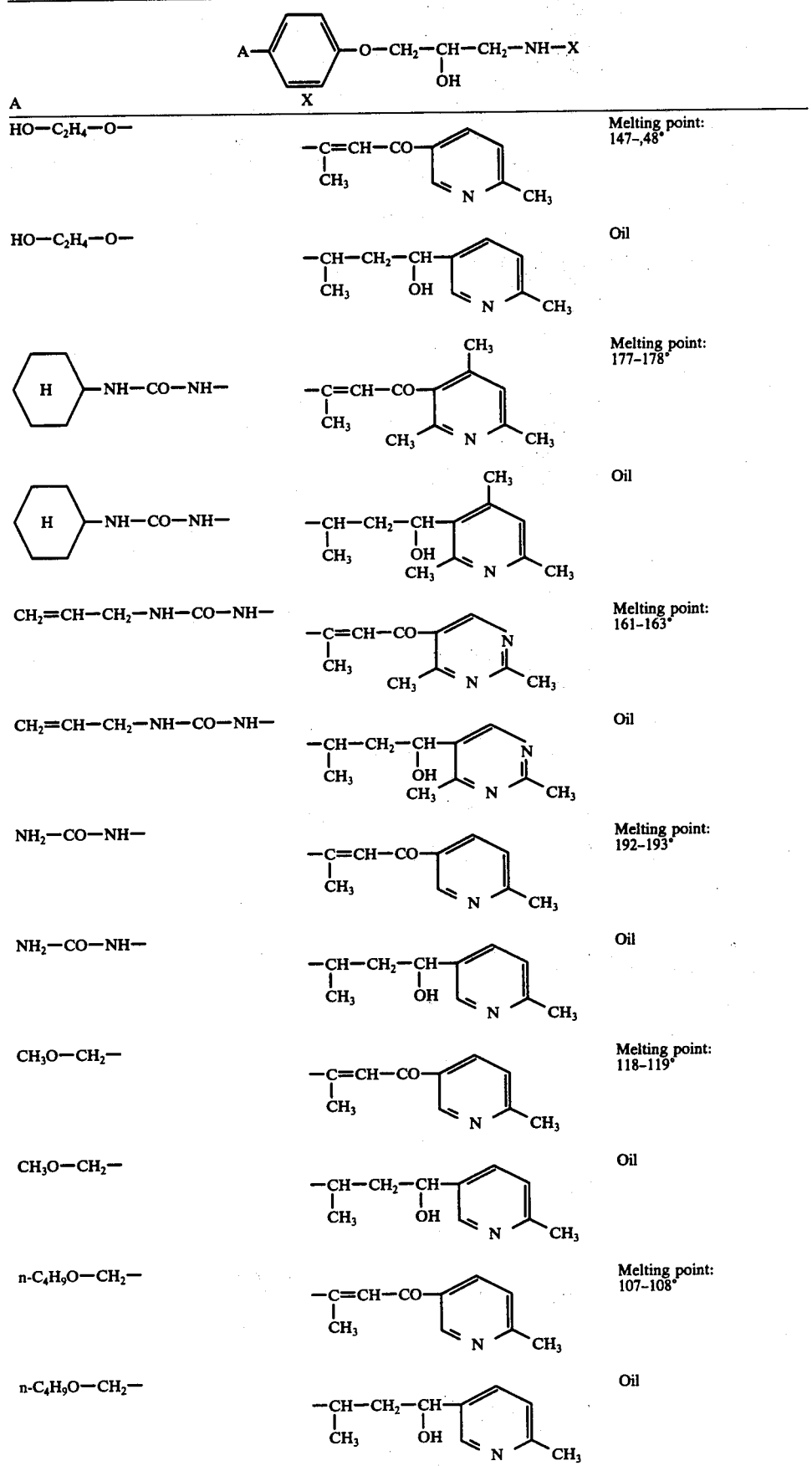

-continued $$A-\!\!\left\langle\!\!\!\bigcirc\!\!\!\right\rangle\!\!-O-CH_2-CH-CH_2-NH-X$$
$$\phantom{A-\bigcirc-O-CH_2-}OH$$

| A | X | |
|---|---|---|
| i-C$_3$H$_7$—NH—CO—NH— | 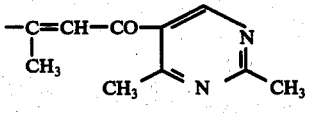 | Melting point: 165–167° |
| i-C$_3$H$_7$—NH—CO—NH— | 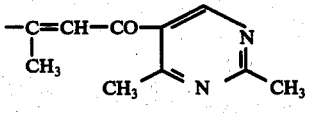 | Oil |
| 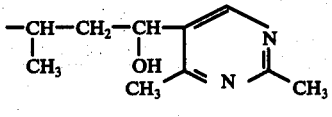 | 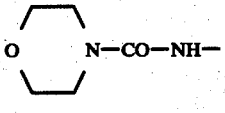 | Melting point: 185–188° |
| 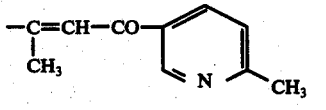 | 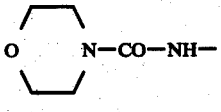 | Oil |
| CH$_3$O—(CH$_2$)$_4$—O— | 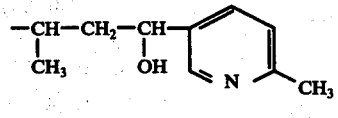 | Melting point: 105–106° |
| CH$_3$O—(CH$_2$)$_4$—O— | 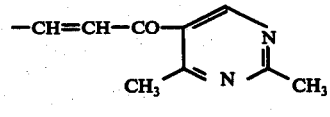 | Melting point: 109–110° |
| CH$_3$O—CH$_2$— | 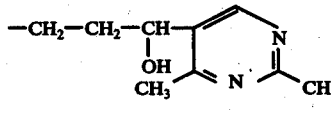 | Oil |
| C$_2$H$_5$O—C$_2$H$_4$—O— | 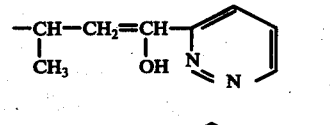 | Melting point: 124–125° |
| C$_2$H$_5$O—C$_2$H$_4$—O— | 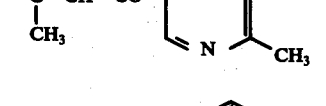 | Oil |
| C$_2$H$_5$O—C$_2$H$_4$—O— | 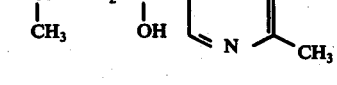 | Oil |
| CH$_3$O—CH$_2$ | 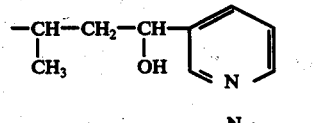 | Oil |
| C$_2$H$_5$O—C$_2$H$_4$O— | 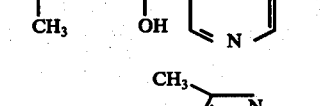 | Oil |

Preparation of the starting diketones

The 6-methylnicotinoyl-acetone which is mentioned as the starting substance in Example 6, can be obtained in a known manner from α-picoline-5-carboxylic acid ethyl ester and acetone, or from 5-acetyl-α-picoline (prepared in accordance with Angew. Ch. 67, page 398) and ethyl acetate:

270 g of 5-acetyl-α-picoline, 5 l of anhydrous toluene, 387 g of ethyl acetate and 537 g of potassium tert.-butylate are stirred at 40° for 20 hours and the mixture is subsequently decomposed by means of a mixture of 3 l of ice water and 288 ml of acetic acid. 283.5 g of 6-methyl-nicotinoyl-acetone, boiling point 108°-117°/0.2 mm Hg, which rapidly crystallises and, after recrystallisation from ligroin, melts at 57°-58°, is obtained in the usual manner from the toluene solution.

The following, inter alia, are obtained in a corresponding manner:

2,4-dimethyl-5-pyrimidylcarbonyl-acetone Melting point:65°-66°

2,4,6-trimethyl-nicotinoyl-acetone Oil, boiling point 98°-107°/0.2 mm Hg 1,5-dimethyl-4-pyrazolylcarbonyl-acetone Oil, boiling point 108°-110°/0.1 mm Hg 4-methyl-5-pyrimidylcarbonyl-acetone, Melting point:52°-54°

2-methyl-4-ethyl-5-pyrimidylcarbonyl-acetone, Melting point:35°-37°

2-thenoyl-acetone, — Melting point:32°-33°

2,4-dimethyl-5-thiazolylcarbonyl-acetone Oil, boiling point 93°-98°/0.15 mm Hg 2,5-dimethyl-3-thenoyl-acetone Oil, boiling point 104°-111°/0.1 mm Hg 3-pyridazinylcarbonyl-acetone — Melting point:110°-112°

Preparation of the starting amines

The following substances are obtained by reacting the phenols

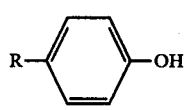

with epichlorohydrin and then with ammonia in the manner described in Example 1 (if R contains a urea group >N—CO—NH—, the distillation is replaced by recrystallisation):

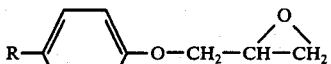

| R | | |
|---|---|---|
| HO—C₂H₄—O— | Melting point: 48–52° (crude) | Melting point: 104–106° |
| CH₃O—CH₂— | Oil, boiling point 105–106°/0.1 mm Hg | Melting point: 59–60° |
| C₂H₅O—CH₂— | Oil, boiling point 120–124°/0.1 mm Hg | Melting point: 54–56° |
| n-C₄H₉O—CH₂ | Oil, boiling point 124–130°/0.1 mm Hg | Melting point: 66–68° |
| H₂N—CO—NH— | Melting point: 149–150° | Melting point: 141–143° |
| CH₃—NH—CO—NH— | Melting point: 146–147° | Melting point: 151–153° |
| C₂H₅—NH—CO—NH— | Melting point: 148–150° | Melting point: 140–141° |
| i-C₃H₇—NH—CO—NH— | Melting point: 176–177° | Melting point: 150–151°; solid again at 161° and melts again at 216–218° |
| n-C₄H₉—NH—CO—NH— | Melting point: 143–144° | Melting point: 134–136° |
| 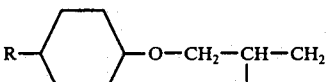 | Melting point: 179–180° | Melting point: 162–163° |
| CH₂=CH—CH₂—NH—CO—NH— | Melting point: 143–144° | Melting point: 145–147° |

The 4-alkoxymethylphenols used as the starting substances are readily accessible from 4-hydroxymethyl-phenol in accordance with Rec. 74, page 1448.

The N-substituted ureidophenols used as the starting substances can be obtained, either from p-aminophenol using (cyclo)-alkylisocyanates or from N-(p-hydroxyphenyl)-O-phenylurethane using primary or secondary amines:

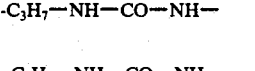

| R | |
|---|---|
| CH₃—NH—CO—NH— | Melting point: 162–164° |
| C₂H₅—NH—CO—NH— | Melting point: 170–173° |
| i-C₃H₇—NH—CO—NH— | Melting point: 164–166° |
| n-C₄H₉—NH—CO—NH— | Melting point: 162–163° |
| CH₂=CH—CH₂—NH—CO—NH— | Melting point: 154–155° |
| —NH—CO—NH— | Melting point: 208–210° |
| | Melting point: 224–227° |
| O⟩N—CO—NH— | |

EXAMPLE 7

2.0 g of 1-(p-[4-methoxybutoxy]-phenoxy)-3-(1-[2-methylpyridyl-5]-1-hydroxybutyl-3-amino)-propan-2-ol (compare Example 6) of the formula

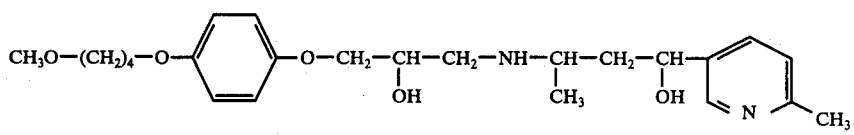

are heated under reflux together with 20 ml of ethanol and 0.50 ml of a 39% strength aqueous formaldehyde solution, for 4 hours. The reaction mixture is evaporated and the residue is taken up in 200 ml of ligroin. Evaporation of the solution, after clarification by means of a little active charcoal, gives 1.8 g of 3-(1-hydroxy-1-[2-methylpyridyl-5]-3-butyl)-5-(4-[4-methoxybutoxy]-phenoxymethyl)-oxazolidine of the formula

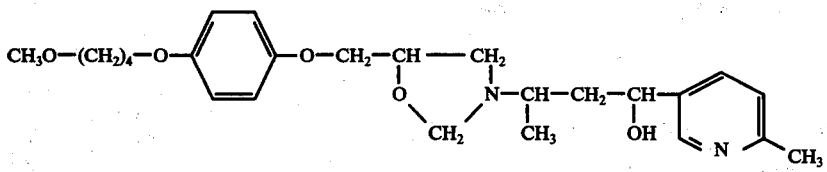

as a colourless oil.

Analysis: (C$_{25}$H$_{36}$N$_2$O$_5$) calculated: C 67.5; H 8.2; N 6.3; O 18.0; found: —67.3; 8.2; 6.2; 18.2.

EXAMPLE 8

1.33 g. sodium boranate are stirred in 21 ml. anhydrous ethanol at room temperature for 45 minutes and when cooled down to 0° C. a solution of 2.32 g. calcium chloride in 21 ml. anhydrous ethanol is added. This gives a milky mixture and its temperature rises to +15° C. This mixture is then cooled to +5° C. and 3 g. 1-(2-[6-methyl-nicotinoyl]-1-methylvinylamino)-3-(p-[2-n-propoxy-ethoxy]-phenoxy)-propan-2-ol of the formula

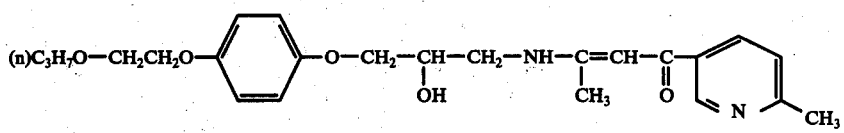

dissolved in 56 ml. anhydrous ethanol is allowed to run into this mixture at this temperature within three minutes' time, the temperature thereby rising as high as 30° C. or so. The mixture is stirred overnight at room temperature, the latter initially having risen as high as 37° C. While stirring vigorously, 5.9 ml. 10 N aqueous sodium hydroxide solution is added which gives a thick paste. Another 12 ml. water are added at once and the whole is stirred vigorously for five minutes. It is then allowed to stand without stirring at room temperature for 30 minutes, filtered with suction over some cellite and the residue is washed with anhydrous ethanol. The filtrate is admixed with 9 ml. glacial acetic acid and evaporated to dryness in vacuo at 50° C. To the evaporated residue there are added 12 ml. 10 N aqueous sodium hydroxide solution and 12 ml. water. The mixture is then extracted with ethyl acetate three times. The combined ethyl acetate phases are washed twice with water, dried with anhydrous sodium sulfate and concentrated in vacuo (20 mm/Hg.), an oil thereby being obtained.

The latter is dissolved in as little 2N hydrochloric acid as possible, and some undissolved residue is filtered off with suction. The filtrate is extracted three times by means of ethyl acetate and the ethyl acetate extracts are rejected. The aqueous solution is adjusted to pH 4.5 with 15% strength sodium carbonate solution, extracted five times with ethyl acetate and the ethyl acetate extracts are rejected. The aqueous solution is then adjusted to pH 8.5 with 15% strength sodium carbonate solution and extracted three times with ethyl acetate. The ethyl acetate phases obtained during the extraction of the aqueous solution having a pH 8.5 are washed three times with water, dried over anhydrous sodium sulfate and concentrated in vacuo at 20 mm. Hg., an oil thereby being obtained.

The oil is once more dissolved in appr. 20 ml. absolute pure ethanol and a little animal charcoal is added. The mixture is then allowed to strain through a fluted double filter and is concentrated in vacuo at 20 mm. Hg., an oil again being obtained. 2.6 g. of this oil are dissolved in 6.1 ml. ethyl acetate and filtered. The filtrate is admixed with 10.6 g. petroleum ether and stirred for about 45 minutes at room temperature, a precipitate being separated out little by little. Thereupon another 15.9 ml. petroleum ether are added and the resulting mixture is stirred at room temperature for 30 minutes and the addition of 26.5 ml. petroleum ether is repeated. The precipitate is drawn off by suction and washed with petroleum ether. Then it is reprecipitated in portions from ethyl acetate by repeatedly adding petroleum ether (in which case 8.7 ml. petroleum ether are added). The product thus obtained is filtered with suction, washed and vacuum-dried at 40° C. Obtained is the 1-(p-[2-n-propoxy-ethoxy]-phenoxy)-3-(1-[2-methyl-pyridyl-5]-1-hydroxy-butyl(3)-amino)-propan-2-ol of the formula

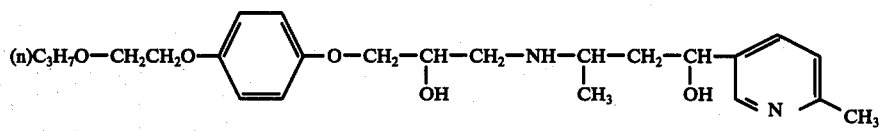

Yield: 89% of theory. Melting point: 72° to 74° C.

It has proved particularly advantageous to convert this compound into the 1,5-naphthalene-disulfonic acid salt for use in pharmaceuticals. This conversion can be effected as follows:

2.5 g of the 1-(p-[2-propoxy-ethoxy]-phenoxy)-3-(1-[2-methyl-pyridyl-5]-1-hydroxy-butyl(3)amino)-propan-2-ol are dissolved in 62.5 ml. ethyl acetate and admixed with a solution 1.65 g. naphthalene disulfonic acid-1,5 in 50 ml. ethyl acetate. The white salt having precipitated is stirred at room temperature for 30 minutes, drawn off by suction, washed with ethyl acetate and vacuum-dried at 40° C. Obtained is the naphthalene disulfonate-1,5 of the 1-(p-[2-propoxy-ethoxy]-phenoxy)-3-(1-[2-methyl-pyridyl-5]-1-hydroxy-butyl(3)amino)-propan-2-ol. On determining the melting point, the salt becomes damp at a temperature of 80° C. and decomposes at 120° C.

The 1-(2-[6-methyl-nicotinoyl]-1-methyl-vinylamino)-3-(p-[2-n-propoxy-ethoxy]-phenoxy)-propan-2-ol of the formula

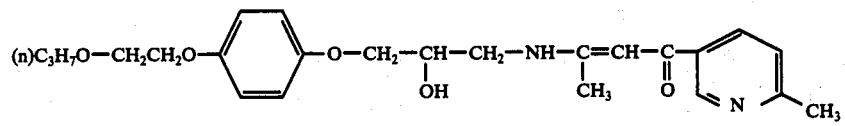

required as reactant can be prepared as follows:
a. 450.0 g. of hydroquinone-monobenzylether and 20.0 g. of potassium tertiary butylate are heated to 105° C. in an autoclave holding 700 ml. 19.4 g. of ethylene oxide each are pressed, while stirring, into the autoclave five times at half-hour's intervals. After a further one-hour stirring at 105° C. the reaction is complete. By recrystallizing the reaction product from isopropanol, 477.5 g. of ethyleneglycol-mono-(4-benzyloxy-phenyl)-ether of the formula

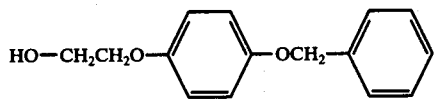

are obtained.
Melting point: 103°–104° C. Analysis: (C$_{15}$H$_{16}$O$_3$) calculated: C 73,7; H 6,6; O 19,7; found: C 73,7; H 6,5; O 19,8.
b. Into 1.0 l. of dimethylformamide there are introduced, whilst cooling with ice, in seven equal portions each a total of 1960 g. of potassium-tertiary butylate, 147 ml. of allylchloride and 427.0 g. of ethyleneglycol-mono-(4-benzyloxy-phenyl)-ether. Stirring is done in the ice bath between the addition of each batch of the three substances for half an hour. Finally, 28 g. of potassium-tertiary butylate and 21 ml. of allylchloride each are added twice in the same manner, after which the ethyleneglycol-mono-(4-benzyloxy-phenyl)-ether is no longer detectable by way of thin-layer chromatography. The reaction mixture is poured into 5 l. of water, small amounts of readily volatile substance are removed by distillation with steam and the whole is cooled with stirring. By filtering with suction, washing with water and drying there are obtained 504.5 g. of crude hydroquinonemono-benzyl-mono-(β-allyloxy-ethyl)-ether of the formula

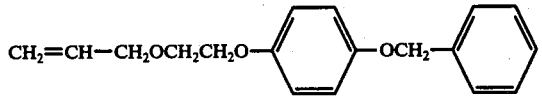

melting at 39° to 42° C. which can be processed without purification.
c. Into a VA-4-(high-grade steel) autoclave holding 700 ml. there are hydrogenised in the presence of 7 g. of Raney-nickel (H$_2$-pressure: 50 metric atmospheres plus pressure) 60 g. of crude hydroquinone-mono-benzyl-mono-(β-allyloxyethyl)-ether dissolved in 400 ml. of methanol. Half of the calculated amount of hydrogen is taken up at room temperature within half an hour, the remainder at 50° C. within five hours. The reaction solution is separated from the nickel and evaporated under reduced pressure. Distillation of the residue gives 37.9 g. of p-(2-n-propoxy-ethoxy)-phenol of the formula

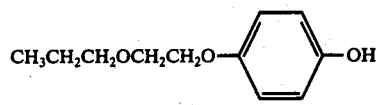

which is a colorless oil having a boiling point of 141° to 148° C./0.1 mm. Hg.
Analysis: (C$_{11}$H$_{16}$O$_3$) calculated: C 67,3 H 8,2 O 24,5 found: C 67,1 H 8,3 O 24,6
d. 39.2 g. of p-(2-n-propoxy-ethoxy)-phenol, 70 ccm. dioxane and 11.8 g. of pulverised potassium hydroxide are stirred at 100° C. for half an hour. The resultant solution is introduced dropwise into a boiling mixture of 93 g. of epichlorohydrin and 200 ml. of butanon-2 over the course of three hours. Heating being continued for 1 hour, the readily volatile substances are distilled off under reflux to 60° C./20 mm. Hg., the residue is removed by stirring with 300 ml. of toluene and the clear toluene solution evaporated under reduced pressure at 60° C./20 mm. Hg. Obtained are 46.9 of crude p-(2-n-propoxy-ethoxy)-phenyl-glycidyl-ether of the formula

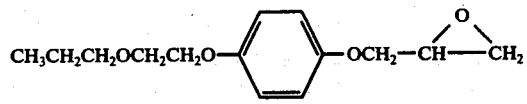

being suitable for immediate further use. Its distillation gives 43.2 g. of the pure compound in the form of a colorless oil having a boiling point of 136° to 145° C./0.05 mm./Hg.
e. 150 ml. of ammonia are added, while stirring, to 46.9 g. of crude p-(2-n-propoxy-ethoxy)-phenyl-glycidyl-ether together with 150 ml. of methanol in an autoclave holding half a liter within a few minutes. The mixture is heated to 70° C. for six hours, an atmosphere excess pressure having set in. The reaction solution is evaporated under reduced pressure and the residue recrystallized from 200 ml. of toluene.
Obtained are 46.8 g. of 1-(p-[2-n-propoxy-ethoxy]-phenoxy)-3-amino-propan-2-ol of the formula

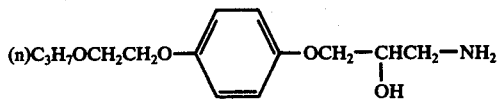

melting at 77° to 79° C.
The melting point is raised to 80°–80.5° C. by distilling the substance (b.p. 158° to 169° C./0.1 mm. Hg.) prior to its recrystallization.

Analysis: ($C_{14}H_{22}NO_3$) calculated: C 62,4; H 8,6; N 5,2; O 23,8; found: C 62,4; H 8,7; N 5,2; O 23,9.

f. 2.69 g. of 1-[2-n-propoxy-ethoxy]-phenoxy)-3-amino-propan-2-ol, 1.77 g. of 6-methyl-nicotinoyl-acetone together with 30 ml. of toluene are heated to the boil for two hours. While doing this, 5 ml. of the mixture are distilled off slowly. By cooling, filtering with suction and drying the solution, one obtains 3.70 g. of the 1-(2-[6-methyl-nicotinoyl]-1-methyl-vinylamino)-3-(p-[2-n-propoxy-ethoxy]-phenoxy)-propan-2-ol.

Melting point: 106°–107° C Analysis: $C_{24}H_{32}N_2O_5$ calculated: C 67,3; H 7,5; N 6,5; O 18,7; found: C 67,2; H 7,5; N 6,5; O 18,9.

What we claim is:

1. A compound of the formula $$A-\langle\text{ring}\rangle-O-CH_2-\underset{OH}{CH}-CH_2-NH-\underset{R_1}{CH}-CH_2-\underset{OH}{CH}\langle B\rangle$$

wherein A is —$CH_2$—alkoxy, —O—alkoxyalkyl, —O—hydroxyalkyl, —NH—CO—N($R_2$)—$R_3$ or $$-(CH_2)_2-[(-CH_2-)_{(2-m)}\{(-O-)_{(2-p)}$$
$$(-S-)_{(p-1)}\}_{(m-1)(2-n)}-(CH_2)_2-]$$
$$-N-$$
$$-CO-$$
$$-NH$$

$R_1$ is —H or methyl;

each of $R_2$ and $R_3$ is, independently, —H, alkyl, alkenyl or cycloalkyl;

each of m, n and P is a positive whole number of at most 2; and ring B is optionally substituted by up to three methyl substituents; each alkyl having from 1 to 4 carbon atoms, each alkoxy having from 1 to 4 carbon atoms, each alkenyl having 3 or 4 carbon atoms and cycloalkyl having from 5 to 7 carbon atoms;

or a pharmaceutically-acceptable acid-addition salt thereof.

2. A compound according to claim 1 wherein A is —$CH_2$-alkoxy, —O-alkoxyalkyl or -O-hydroxyalkyl.

3. A pharmaceutically-acceptable β-adrenergic-blocking composition comprising diluent or excipient and an effective concentration of a compound according to claim 1.

4. A pharmaceutically-acceptable composition comprising diluent or excipient and a β-adrenergic-blocking-effective concentration of a compound according to claim 2.

5. A compound according to claim 1 which is 1-(p-methoxybutoxyphenoxy)-3-(1-hydroxy-1-[pyridyl-3]-butyl-3-amino)propan-2-ol or a pharmaceutically-acceptable acid-addition salt thereof.

6. A compound according to claim 1 which is 1-(p-[2-propoxyethoxy]phenoxy)-3-(1-[2-methylpyridyl-5]-1-hydroxybutyl-3-amino)propan-2-ol or a pharmaceutically-acceptable acid-addition salt thereof.

7. A compound according to claim 1 which is 1-(p-2-hydroxyethoxy]phenoxy)-3(1-[2-methylpyridyl-5]-1-hydroxybutyl-3-amino)propan-2-ol or a pharmaceutically-acceptable acid-addition salt thereof.

8. A compound according to claim 1 which is 1-(p-cyclohexylureidophenoxy)-3-[pyridyl-3]-1-hydroxybutyl-3-amino)propan-2-ol or a pharmaceutically-acceptable acid-addition salt thereof.

9. A compound according to claim 1 which is 1-(p-cyclohexylureidophenoxy)-3-(1-[2-methylpyridyl-5]-1-hydroxybutyl-3-amino)propan-2-ol or a pharmaceutically-acceptable acid-addition salt thereof.

10. A compound according to claim 1 which is 1-(p-ethoxymethylenephenoxy)-3-(1-[pyridyl-3]-1-hydroxybutyl-3-amino)propan-2-ol or a pharmaceutically-acceptable acid-addition salt thereof.

11. A compound according to claim 1 which is 1-(p-ethylureidophenoxy)-3-(1-[pyridyl-3]-1-hydroxybutyl-3-amino)propan-2-ol or a pharmaceutically-acceptable acid-addition salt thereof.

12. A compound according to claim 1 which is 1-(p-ethoxyethoxyphenoxy)-3-(1-[pyridyl-3]-1-hydroxybutyl-3-amino)propan-2-ol or a pharmaceutically-acceptable acid-addition salt thereof.

* * * * *